United States Patent
Drews et al.

(10) Patent No.: US 11,478,363 B2
(45) Date of Patent: Oct. 25, 2022

(54) HYDRAULIC PROSTHETIC KNEE WITH RESISTANCE CHANGE MECHANISM AT HYPEREXTENSION

(71) Applicant: College Park Industries, Inc., Warren, MI (US)

(72) Inventors: Jacob Drews, Washington, MI (US); Aaron Taszreak, China, MI (US)

(73) Assignee: College Park Industries, Inc., Warren, MI (US)

( * ) Notice: Subject to any disclaimer, the term of this patent is extended or adjusted under 35 U.S.C. 154(b) by 0 days.

(21) Appl. No.: 16/943,217

(22) Filed: Jul. 30, 2020

(65) Prior Publication Data

US 2021/0030568 A1    Feb. 4, 2021

Related U.S. Application Data

(60) Provisional application No. 62/880,233, filed on Jul. 30, 2019.

(51) Int. Cl.
| | | |
|---|---|---|
| *A61F 2/64* | (2006.01) | |
| *A61F 2/74* | (2006.01) | |
| *A61F 2/50* | (2006.01) | |

(52) U.S. Cl.
CPC .............. *A61F 2/64* (2013.01); *A61F 2/748* (2021.08); *A61F 2/74* (2021.08); *A61F 2/744* (2021.08); *A61F 2002/5006* (2013.01)

(58) Field of Classification Search
CPC .... A61F 2/64; A61F 2/74; A61F 2/744; A61F 2/748; A61F 2002/5006
See application file for complete search history.

(56) References Cited

U.S. PATENT DOCUMENTS

| | | | | |
|---|---|---|---|---|
| 3,605,960 A | * | 9/1971 | Singer | F16F 9/48 188/314 |
| 3,774,634 A | * | 11/1973 | Bonney | F16K 11/072 251/283 |
| 3,799,159 A | | 3/1974 | Scott | |
| 3,871,032 A | * | 3/1975 | Karas | A61F 2/6607 623/47 |
| 4,010,829 A | * | 3/1977 | Naito | B60G 17/08 188/278 |

(Continued)

FOREIGN PATENT DOCUMENTS

GB    1380428 A    1/1975

*Primary Examiner* — Jacqueline Woznicki
(74) *Attorney, Agent, or Firm* — Dinsmore & Shohl LLP

(57) ABSTRACT

A prosthetic knee includes a hydraulic resistance system with an extension hydraulic circuit and a flexion hydraulic circuit. The flexion hydraulic circuit includes a switchable resistance assembly with a mechanical switch. The mechanical switch has an engaged position and a released position. The switchable resistance assembly provides a first level of hydraulic resistance when the mechanical switch is in the released position and a second level of hydraulic resistance when the mechanical switch is in the engaged position, the second level being less than the first level. The mechanical switch moves to the engaged position when the hydraulic resistance element reaches a predetermined extension position and moves back to the released position when fluid flow falls below a predetermined threshold.

37 Claims, 15 Drawing Sheets

(56) References Cited

U.S. PATENT DOCUMENTS

| | | | |
|---|---|---|---|
| 4,212,087 A * | 7/1980 | Mortensen | A61F 2/64 188/313 |
| 5,376,137 A | 12/1994 | Shorter et al. | |
| 5,383,939 A * | 1/1995 | James | A61F 2/70 623/44 |
| 5,948,021 A | 9/1999 | Radcliffe | |
| 6,106,560 A | 8/2000 | Boender | |
| 6,113,642 A | 9/2000 | Petrofsky et al. | |
| 6,182,697 B1 * | 2/2001 | Parker | F15B 13/01 91/468 |
| 6,517,585 B1 | 2/2003 | Zahedi et al. | |
| 7,909,885 B2 | 3/2011 | Andrysek | |
| 7,985,265 B2 * | 7/2011 | Moser | A61F 2/6607 623/47 |
| 8,574,312 B2 * | 11/2013 | Moser | A61F 2/6607 623/47 |
| 9,402,748 B2 * | 8/2016 | Boender | A61F 2/68 |
| 9,975,249 B2 * | 5/2018 | Herr | B62D 57/032 |
| 2004/0054423 A1 * | 3/2004 | Martin | A61F 2/6607 623/24 |
| 2004/0083007 A1 * | 4/2004 | Molino | A61F 2/68 623/44 |
| 2004/0117036 A1 * | 6/2004 | Townsend | A61F 2/66 623/38 |
| 2005/0015156 A1 * | 1/2005 | Hikichi | A61F 2/64 623/44 |
| 2006/0136072 A1 * | 6/2006 | Bisbee, III | A61F 2/70 623/24 |
| 2006/0206043 A1 * | 9/2006 | Yakimovich | A61F 5/0125 602/5 |
| 2006/0235544 A1 * | 10/2006 | Iversen | A61F 2/70 623/47 |
| 2007/0027555 A1 * | 2/2007 | Palmer | A61F 2/70 623/44 |
| 2007/0050044 A1 * | 3/2007 | Haynes | A61F 2/64 623/44 |
| 2007/0208431 A1 | 9/2007 | Bisinger et al. | |
| 2008/0228287 A1 * | 9/2008 | Ninomiya | A61F 2/60 623/47 |
| 2008/0300692 A1 * | 12/2008 | Moser | A61F 2/70 623/26 |
| 2009/0319055 A1 * | 12/2009 | Iversen | A61F 2/68 623/49 |
| 2010/0023133 A1 * | 1/2010 | Fairbanks | A61F 2/70 623/24 |
| 2010/0138000 A1 | 6/2010 | Palmer et al. | |
| 2010/0191347 A1 * | 7/2010 | Pusch | A61F 2/60 600/595 |
| 2011/0087339 A1 * | 4/2011 | Pusch | A61F 2/64 623/43 |
| 2011/0098828 A1 * | 4/2011 | Balboni | A61F 2/60 623/40 |
| 2011/0307078 A1 * | 12/2011 | Boender | A61F 2/68 623/26 |
| 2012/0119123 A1 * | 5/2012 | Battlogg | F16F 9/46 251/129.01 |
| 2012/0191219 A1 * | 7/2012 | Boender | A61F 2/68 623/44 |
| 2012/0226364 A1 * | 9/2012 | Kampas | A61F 2/6607 623/24 |
| 2013/0204395 A1 * | 8/2013 | Gramnaes | A61F 2/60 623/26 |
| 2014/0249652 A1 * | 9/2014 | Taszreak | A61F 2/6607 623/50 |
| 2015/0202057 A1 * | 7/2015 | Zahedi | A61F 2/60 623/47 |
| 2015/0328020 A1 * | 11/2015 | Clausen | A61F 2/72 623/25 |
| 2016/0296347 A1 | 10/2016 | Boender | |
| 2017/0336273 A1 * | 11/2017 | Elangovan | A43B 17/18 |
| 2018/0036148 A1 * | 2/2018 | Lincoln | A61F 2/64 |
| 2018/0036149 A1 * | 2/2018 | Harris | A61F 2/80 |
| 2018/0098864 A1 * | 4/2018 | Auberger | A61F 2/64 |
| 2018/0133030 A1 * | 5/2018 | Seifert | A61F 5/0125 |
| 2018/0235516 A1 * | 8/2018 | Morris Bamberg | G01C 22/006 |
| 2018/0235830 A1 * | 8/2018 | Rokosz | A61H 3/00 |
| 2018/0256371 A1 * | 9/2018 | Palmer | A61F 2/70 |
| 2018/0256380 A1 * | 9/2018 | Pusch | A61F 5/0102 |
| 2019/0046336 A1 | 2/2019 | Zahedi et al. | |
| 2020/0237531 A1 * | 7/2020 | Prince | A61F 2/70 |
| 2021/0015638 A1 * | 1/2021 | Taszreak | A61F 2/50 |
| 2021/0030568 A1 * | 2/2021 | Drews | A61F 2/64 |
| 2021/0196483 A1 * | 7/2021 | Boiten | A61F 2/748 |

\* cited by examiner

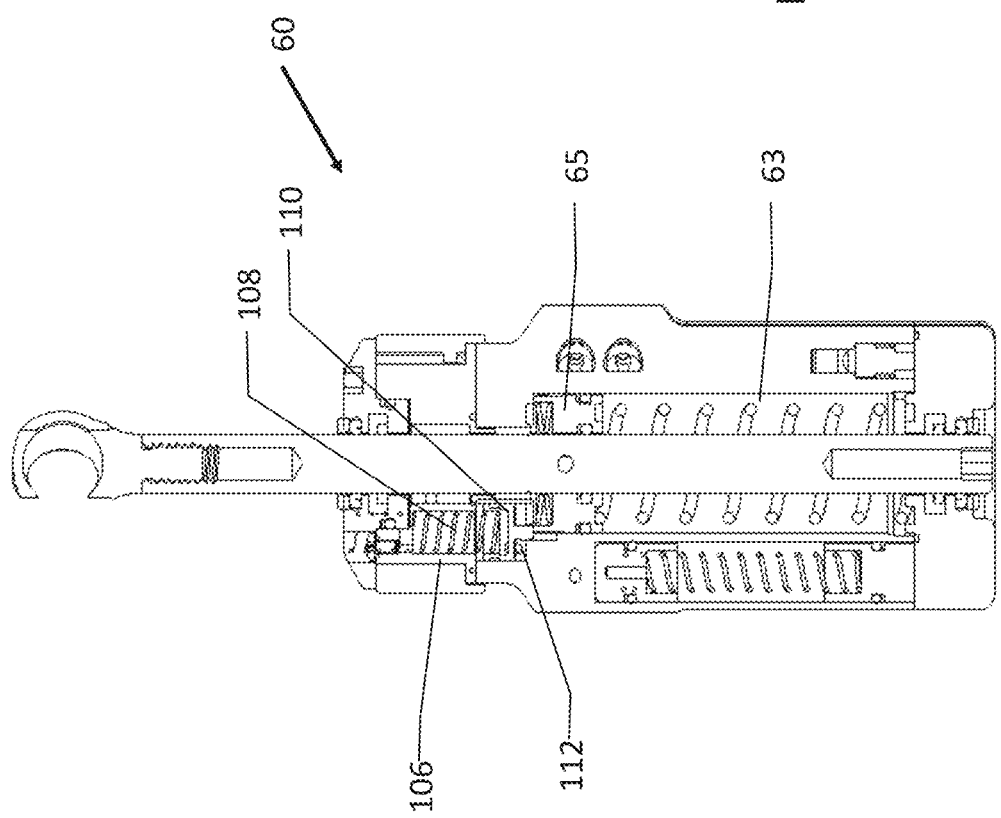

HYDRAULIC PROSTHETIC KNEE WITH RESISTANCE CHANGE MECHANISM AT HYPEREXTENSION

CROSS REFERENCE TO RELATED APPLICATIONS

This application claims priority to U.S. Provisional Patent Application Ser. No. 62/880,233, filed Jul. 30, 2019, the entire content of which is incorporated herein by reference.

FIELD OF THE INVENTION

The present invention relates generally to prosthetic knees and, more specifically, to a hydraulic prosthetic knee with resistance changes.

BACKGROUND OF THE INVENTION

Prosthetic knees provide support to a user and also allow articulation such that the user may walk and swing the leg, as well as to sit with the leg bent. Often, prosthetic knees include damping to control the motion of the lower leg relative to the upper leg. Highly active users benefit from a prosthetic knee with higher levels of control and performance.

SUMMARY OF THE INVENTION

The present invention provides a prosthetic knee wherein the resistance to flexion is mechanically switched to a lower level when the knee reaches a hyperextension position and back to a higher level when flexion motion falls below a threshold, thereby providing support once flexion ceases or slows to a certain level.

A first embodiment of a prosthetic knee includes an upper thigh portion and a lower shin portion connected by a joint. The joint allows the shin portion to articulate, between an extended position wherein the thigh portion and the shin portion are generally aligned along a leg axis and a bent position wherein the shin portion is angled rearwardly with respect to the thigh portion, movement from the extended position toward the bent position defined as flexion and movement from the bent position toward the extended position defined as extension. A hydraulic resistance system is operable to selectively provide hydraulic resistance to flexion and extension of the knee. The hydraulic resistance system includes a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension. An extension hydraulic circuit connects the first and second fluid chambers and has a check valve operable to allow flow from the first fluid chamber to the second fluid chamber and to substantially block flow from the second fluid chamber to the first fluid chamber. The extension hydraulic circuit further includes a resistance element operable to provide hydraulic resistance to the flow from the first fluid chamber to the second fluid chamber. A flexion hydraulic circuit connects the first and second fluid chambers and has a check valve operable to allow flow from the second fluid chamber to the first fluid chamber and to substantially block flow from the first fluid chamber to the second fluid chamber. A switchable resistance assembly includes a mechanical switch, the mechanical switch having an engaged position and a released position. The switchable resistance assembly provides a first level of hydraulic resistance to flow from the second fluid chamber to the first fluid chamber when the mechanical switch is in the released position and a second level of hydraulic resistance to flow from the second fluid chamber to the first fluid chamber when the mechanical switch is in the engaged position, the second level being less than the first level. The mechanical switch moves to the engaged position when the hydraulic resistance element reaches a predetermined extension position and moves back to the released position when flow from the second chamber to the first chamber falls below a predetermined threshold.

A second embodiment of a prosthetic knee includes an upper thigh portion and a lower shin portion connected by a joint. The joint allows the shin portion to articulate, between an extended position wherein the thigh portion and the shin portion are generally aligned along a leg axis and a bent position wherein the shin portion is angled rearwardly with respect to the thigh portion, movement from the extended position toward the bent position defined as flexion and movement from the bent position toward the extended position defined as extension. A hydraulic resistance system is operable to selectively provide hydraulic resistance to flexion and extension of the knee. The hydraulic resistance system includes a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension. An extension hydraulic circuit connects the first and second fluid chambers and has a check valve operable to allow flow from the first fluid chamber to the second fluid chamber and to substantially block flow from the second fluid chamber to the first fluid chamber. The extension hydraulic circuit further includes a resistance element operable to provide hydraulic resistance to the flow from the first fluid chamber to the second fluid chamber. A first flexion hydraulic circuit connects the first and second fluid chambers and has a check valve operable to allow flow from the second fluid chamber to the first fluid chamber and to substantially block flow from the first fluid chamber to the second fluid chamber. The flexion hydraulic circuit further has a resistance element operable to provide hydraulic resistance to the flow from the second fluid chamber to the first fluid chamber. A second flexion hydraulic circuit connects the first and second fluid chambers and includes a check valve operable to allow flow from the second fluid chamber to the first fluid chamber and to substantially block flow from the first fluid chamber to the second fluid chamber. The flexion hydraulic circuit further having a resistance element operable to provide hydraulic resistance to the flow from the second fluid chamber to the first fluid chamber. The resistance element of the first flexion hydraulic circuit provides a first level of hydraulic resistance and the resistance element of the second flexion hydraulic circuit provides a second level of hydraulic resistance, the second level being less than the first level. A mechanical switch has an engaged position and a released position, the mechanical switch in the engaged position operable to allow flow through the second flexion hydraulic circuit, thereby allowing flow during flexion through the second flexion circuit, the mechanical switch in the released position substantially blocking the second flexion hydraulic circuit, thereby limiting flow during flexion to the first flexion hydraulic circuit. The mechanical switch moves to the engaged position when the hydraulic resistance element reaches a predetermined extension position and moves back to the released position when flow from the second chamber to the first chamber falls below a predetermined threshold.

In some examples, the embodiments of the knee are completely mechanical with no electronically controlled valves or switches. In some examples the hydraulic resistance element is a hydraulic cylinder with a cylinder body having a bore defined therein, a piston having a piston head separating the first fluid chamber from the second fluid chamber, and a piston rod connected to the upper thigh portion, the cylinder body being connected to the lower shin portion.

In some examples, the flexion and extension resistance levels are adjustable.

In some examples, the upper thigh portion comprises an upper bone subassembly.

In some examples, the hydraulic resistance element comprises a piston and the mechanical switch comprises a body and a plunger, the plunger contacting the piston when the hydraulic resistance element reaches the predetermined extension position.

In some examples, the predetermined extension position is a hyperextension position.

In some examples, the knees further include an adjustment mechanism for adjusting an amount of force required to engage the mechanical switch.

In some examples, a single check valve is the check valve of the first flexion hydraulic circuit and is the check valve of the second flexion hydraulic circuit.

According to a further embodiment, a method of controlling a prosthetic knee includes providing a prosthetic knee with an upper thigh portion, a lower shin portion and a joint connecting them. The joint allows the shin portion to articulate between an extended position wherein the thigh portion and the shin portion are generally aligned along a leg axis and a bent position wherein the shin portion is angled rearwardly with respect to the thigh portion, movement from the extended position toward the bent position defined as flexion and movement from the bent position toward the extended position defined as extension. A hydraulic resistance element is operable to selectively provide hydraulic resistance to flexion and extension. The method includes providing a first level of hydraulic resistance to flexion when the prosthetic knee is in a stance mode with the knee moving from forward of a user's body to rearward of the user's body, mechanically switching the hydraulic resistance to a second level when the prosthetic knee reaches an extended position at a terminal position of the stance mode, the second level of resistance being less than the first level of resistance, the second level of resistance allowing flexion such that the user can swing the knee forwardly in a swing mode in an at least partially bent position, and mechanically switching the level of hydraulic resistance back to the first level when the knee stops moving in flexion. In some examples, the method may utilize any of the embodiments or examples of the knee.

BRIEF DESCRIPTION OF THE DRAWINGS

FIG. 8 is a another cross-sectional view of the hydraulic cylinder of FIG. 5;
FIG. 1013 is a schematic showing the plunger of the mechanical switch being depressed.

DETAILED DESCRIPTION

As known to those of skill in the art, prosthetic knees must provide different levels of support for a user depending on the phase of the gait of the user. A prosthetic knee typically has an upper thigh portion connected to a lower shin portion by a joint. The joint allows the shin portion to articulate, between an extended position wherein the thigh portion and the shin portion are generally aligned along a leg axis and a bent position wherein the shin portion is angled rearwardly with respect to the thigh portion. Movement from the extended position toward the bent position is defined as flexion and movement from the bent position toward the extended position is defined as extension. A hydraulic resistance system is operable to selectively provide hydraulic resistance to flexion and extension of the knee.

Figure 1:
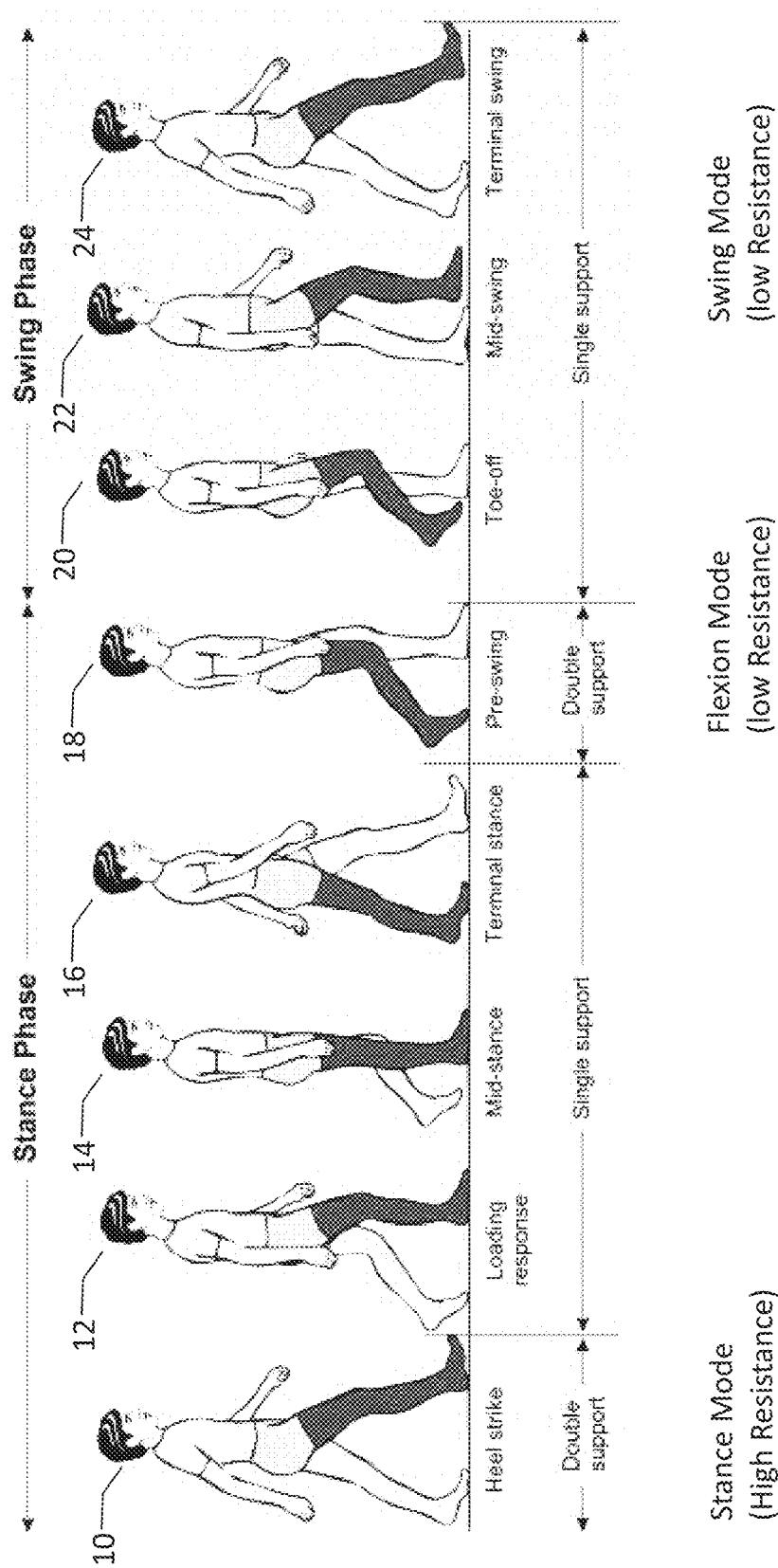
FIG. 1 is a schematic illustrating the phases of gait for a person walking.

FIG. 1 illustrates the phases of gait for a person walking. These phases will be described with respect to the user's right leg, which is the foreground leg in the Figure. In the Figure, the right leg represents a leg including a prosthetic knee. Beginning at the left of FIG. 1, the user is shown at 10 starting a stride with the leg fully extended and in the forwardmost position relative to the user's body. The heel strikes the walking surface in this position and may be considered a heel strike position. As the user moves forward, a load is placed on the leg at the position shown at 12 and then the leg reaches a position directly under the user's body as shown at 14, known as a mid-stance position.

Continuing forward, the leg reaches a rearwardmost position, as shown at 16, referred to as a terminal stance. How far forwardly the leg is in position 10 and how far rearwardly the leg is in position 16 depends on the user's stride length, but these positions are considered to be the forwardmost and rearwardmost positions, respectively, for a given stride.

The user then moves their thigh forwardly, as shown at 18. Preferably, the knee joint is allowed to flex such that the forward motion of the thigh causes the shin portion of the leg to flex upwardly into a partially bent position. As the user continues swinging their thigh forward, as shown at 20, the knee continues to flex and the toe is lifted, referred to as toe-off. As the thigh continues forward of the body, movement of the thigh slows causing the shin portion to swing forwardly, due to momentum. This is shown at 22 and is referred to as a mid-swing position. At 24, the thigh has reached its forwardmost position and the shin portion has swung forward to a fully extended position, wherein the shin and thigh are generally aligned along a leg axis. This is referred to as the terminal swing position, and occurs just before heel strike, as in position 10.

The amount of support provided by the leg should be high, corresponding to a high level of resistance to knee flexion, when the user reaches the heel strike position and should remain high as the leg is loaded and the user moves through position 12 to the mid-stance position 14 and to the terminal stance position 16. However, beginning just after the terminal stance position 16, the leg is no longer required to support the user. Instead, it is desirable that the knee have a very low level of resistance to flexion such that the knee allows the shin portion to easily swing upward as the user moves into the pre-swing position 18 and toe-off position 20. In the mid-swing position 22, the knee allows extension so that the shin portion can swing forwardly. Normally, the leg does not need to provide support in this position, since it is not contacting the ground. When the leg reaches the terminal swing position 24, the leg needs to again be ready to provide support.

If the user stumbles or suddenly shortens their stride, such that the user tries to put weight on the leg in any of positions 18-22, a typical prosthetic knee may collapse because the flexion resistance is low to allow the shin to easily flex towards the thigh.

In accordance with embodiments of the present invention, a prosthetic knee switches from high flexion resistance at the terminal stance position, when the knee slightly hyperextends, to a low flexion resistance to allow the knee to flex during the swing phase of the gait. Then, when flexion of the knee stops or the rate of flexion falls below a threshold, the prosthetic knee switches back to the high flexion resistance, allowing the leg to bear the user's weight. This normally happens at position 24 when the knee has stopped flexing and begun to extend. The knee is then ready to bear weight. However, the embodiments also provide support for the user in other situations. For example, if a user stumbles and stops moving their thigh forwardly at positions 20 or 22, flexion will slow or stop momentarily as the shin portion stops flexing upwardly, and the knee will switch to the high flexion resistance level. If the user then puts a load on the leg, the leg will provide a high level of support.

Figure 2:
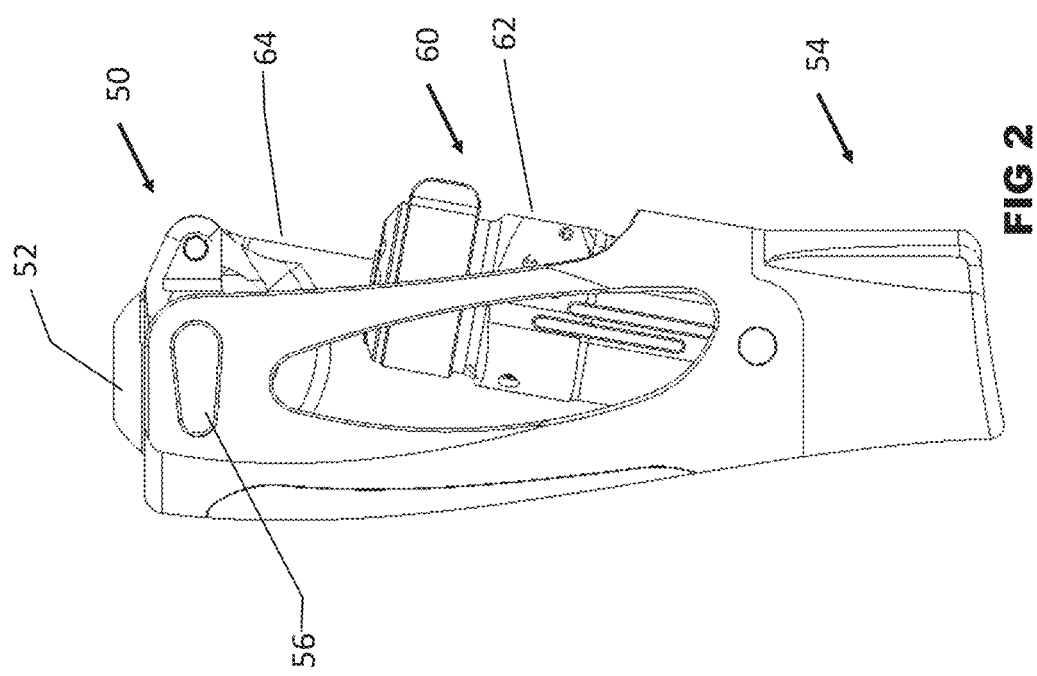
FIG. 2 is a side view of a prosthetic knee according to an embodiment of the present invention.

FIG. 2 illustrates a prosthetic knee 50 according to an embodiment of the present invention. The knee 50 has an upper portion 52 and a lower portion 54 that are connected to each other by a joint 56. In this embodiment, the joint is a pivot joint between the upper portion 52 and lower portion 54. The upper portion 52 may be referred to as a thigh portion as it connects to a user's thigh or thigh prosthetic, typically through a thigh-engaging socket. The lower portion 54 may be referred to as a shin portion. Rearward movement of the lower shin portion 54 causes it to pivot at the joint 56 and move towards the thigh of a user. This is referred to as flexion. Movement in the opposite direction is referred to as extension.

The knee further has a hydraulic resistance system 60 that provides resistance to flexion and extension. The level or resistance depends on a number of factors and may further be adjustable. In the illustrated embodiment, the hydraulic resistance system takes the form of a hydraulic cylinder having a cylinder body 62, a cylindrical bore defined in the body (not shown), a piston having a piston head in the bore and a piston rod 64. In this embodiment, the cylinder body 62 is connected to the lower portion 54 and the piston rod 64 is connected to the upper portion 52 such that flexion motion moves the piston rod 64 into the cylinder body 62 and extension motion extends the piston rod 64 out of the cylinder body 62. The system could be inverted with the cylinder body 62 attached to the upper portion 52 and the piston rod 64 attached to the lower portion 54 or such that motion due to flexion and extension are reversed. As will be clear to those of skill in the art, other types of hydraulic resistance systems may be used, such as curved cylinders and rotary hydraulic dampers. In each case, the damper or resistance system has two parts that move relative to each other causing hydraulic fluid to flow between chambers. Resistance to or blocking of this flow resists or stops motion.

Figure 3:
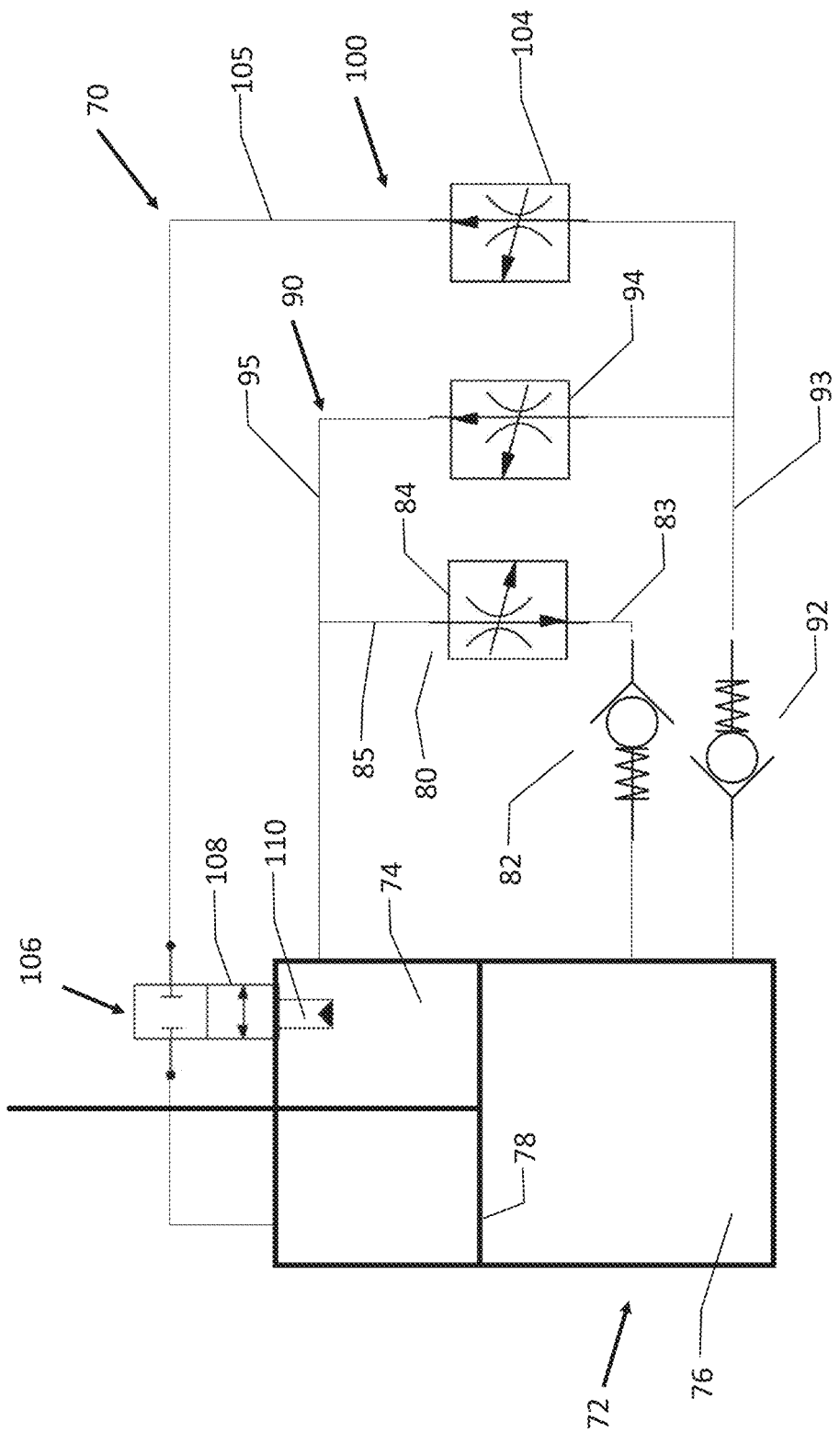
FIG. 3 is a schematic of an embodiment of a hydraulic resistance system for use with the present invention.

FIG. 3 is a schematic of an embodiment of a hydraulic resistance system 70 for use with the present invention. The system 70 includes a hydraulic resistance element 72 with an internal area divided into a first fluid chamber 74 and a second fluid chamber 76 by a head of a piston 78. In the illustrated embodiment, the first chamber 74 is on an upper side of the piston 78 and the second chamber 76 is on a lower side of the piston 78. A system of hydraulic circuits extends between the two chambers such that fluid may flow between the chambers as the piston moves. If the resistance element 72 is a hydraulic cylinder as in FIG. 2, movement of the knee in flexion causes the piston 78 to move downwardly, thereby decreasing the size of the second chamber 76 and increasing the size of the first chamber 74. Extension of the knee causes the opposite; the piston 78 moves upwardly, thereby decreasing the size of the first chamber 74 and increasing the size of the second chamber 76. Ports are typically provided in the fluid chambers for fluid communication with the hydraulic circuits. The hydraulic circuits may share ports and parts of a flow path or may be totally independent, such as with different ports.

An extension hydraulic circuit 80 connects the first and second chambers and has a check valve 82 which is operable to block flow from the second chamber 76 to the first chamber 74 and to allow flow from the first chamber 74 to the second chamber 76. This means that fluid flows through the extension hydraulic circuit 80 when the knee is extending. The extension hydraulic circuit 80 has a resistance element 84 which may resist the flow of fluid. The resistance element 84 may take the form of a valve and may be adjustable, such as by a user or technician for setting the amount of resistance to extension of the knee. The resistance is typically low for this element. The resistance is typically not adjusted or adjustable during stride; it is not actively adjusted. Instead, it is set at the start of or before use and then the resistance setting remains the same for an extended period.

A flexion hydraulic circuit, in this embodiment, takes the form of two circuits. A first flexion hydraulic circuit 90 connects the first and second chambers and has a check valve 92 that is operable to block flow from the first chamber 74 to the second chamber 76 and to allow flow from the second chamber 76 to the first chamber 74. This means that fluid flows through the first flexion hydraulic circuit 90 when the knee is flexing. The first flexion hydraulic circuit 90 has a resistance element 94 which may resist the flow of fluid. The resistance element 94 may take the form of a valve and may be adjustable, but not be actively adjustable such as during a stride.

A second flexion hydraulic circuit 100 also connects the first and second chambers and, in this embodiment, shares the check valve 92 with the first flexion hydraulic circuit. Alternatively, a separate check valve may be used. The second flexion hydraulic circuit has a resistance element 104 that resists flow. Unlike the first flexion hydraulic circuit 90, the second flexion hydraulic circuit 100 includes a mechanical switch 106 that selectably allows or blocks fluid flow. In the illustrated embodiment, the mechanical switch has a body 108 and a plunger 110 extending from the body. When the plunger 110 is depressed into the body 108, the mechanical switch is in an engaged position, which allows flow through the second flexion hydraulic circuit. When the plunger 110 is extended, the switch is in a released position and flow through the second flexion hydraulic circuit 100 is substantially blocked. When this flow is blocked, fluid flow during flexion is limited to the first flexion hydraulic circuit 90. The resistance to flow in the first flexion hydraulic circuit 90 is higher than the resistance to flow in the second flexion hydraulic circuit 100. As such, when the mechanical switch 106 is engaged, thereby allowing flow through the second flexion hydraulic circuit 100, the resistance to flexion is much lower than when the mechanical switch is released and flexion flow is limited to the higher resistance first flexion hydraulic circuit 90. As will be clear from FIG. 3, when the mechanical switch is engaged, and flow is allowed through the second flexion hydraulic circuit 100, fluid may also pass through the first flexion hydraulic circuit 90. However, most flow will be through the lower resistance second flexion hydraulic circuit 100.

In this embodiment, the plunger 110 is depressed when the piston 78 reaches an upper position and contacts the plunger 110. The system is designed such that the piston 78 contacts the plunger 110 with the leg and knee in a fully extended position and hyperextension of the knee causes the piston 78 to depress the plunger 110. This hyperextension may occur at the terminal stance position 16, depending on how the user is loading the leg. The mechanical switch 106 is designed such that once it is depressed, it remains depressed as long as there is flexion fluid flow through the switch and the flow is above a threshold. Once the flow drops below the threshold, the plunger 10 extends, as long as the piston is not in contact. Referring back to FIG. 1, the flexion flow through the switch will drop or stop when the shin starts extending forward, and the knee extends, in positions 22 or 24. This reduction of flow will cause the switch to return to the released position, in which flow in the second flexion hydraulic circuit 100 is blocked and the flexion resistance returns to a level allowing the knee to adequately support the user's weight.

It is noted that certain embodiments of the present invention provide a completely mechanical knee with a completely mechanical flexion and extension resistance system. In these certain embodiments, the levels of flexion resistance are adjusted using mechanical systems and no electronic controls or adjustment are provided. It is also noted that the resistance element of any of the circuits may be formed by orifices or by passages which provide some resistance to flow. Adjustable resistance elements may be used for all or for some. Check valves and resistance elements may be combined in some versions. The mechanical switch 106 may provide the resistance of element 104, such as by sizing an orifice in the switch.

Figure 4:
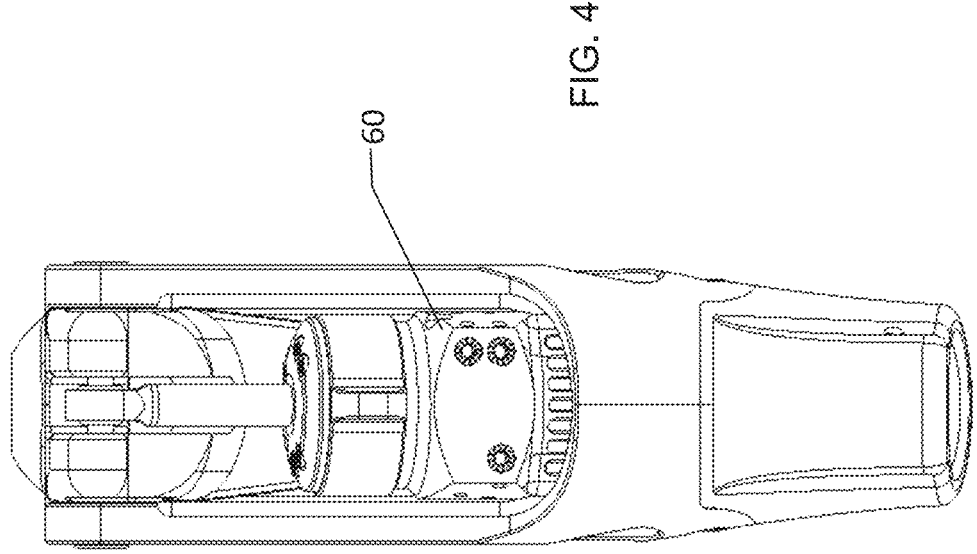
FIG. 4 is a front view of a prosthetic knee according to an embodiment of the present invention.
Figure 5:
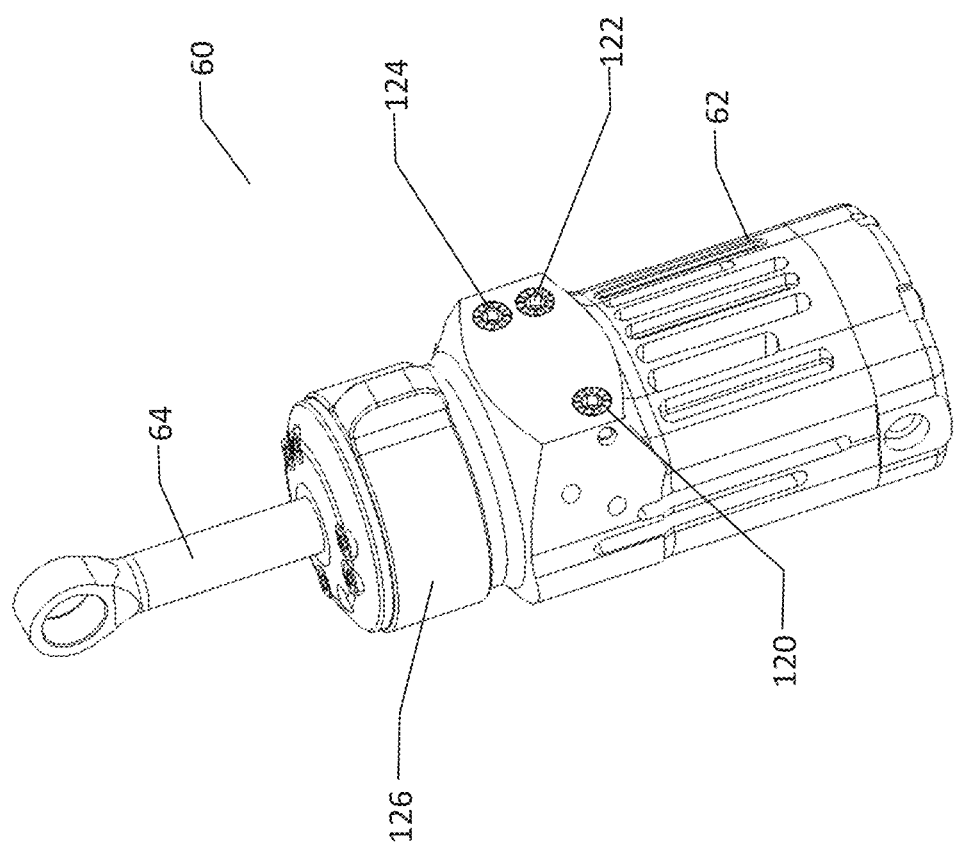
FIG. 5 is a prospective view of an embodiment of a hydraulic cylinder for use with the present invention.

Referring now to FIGS. 4-8, the hydraulic resistance system will be described in more detail. FIG. 4 shows the prosthetic knee of FIG. 2 but from the front, better showing the hydraulic cylinder, which defines the resistance system 60. FIG. 5 shows the hydraulic cylinder 60, having a cylinder body 62 and piston rod 64. The front of the body 62, in this embodiment, includes adjustment fittings which may be engaged with a tool and used to adjust the resistance provided by the resistance elements. Adjustment fitting 120 is used to adjust the resistance element 84 in the extension hydraulic circuit 80 of FIG. 3. Adjustment fitting 122 is used to adjust the resistance element 94 in the first flexion hydraulic circuit 90 of FIG. 3. Adjustment fitting 124 is used to adjust the resistance element 104 in the second flexion hydraulic circuit 100. Certain embodiments of the cylinder 60 may also include a mode selection switch or knob 126. In the illustrated embodiment, the mode selection switch surrounds the piston rod 64 at the upper end of the cylinder body 62 and rotates about the axis of the piston rod to select modes. The modes will be discussed below.

Figure 6:
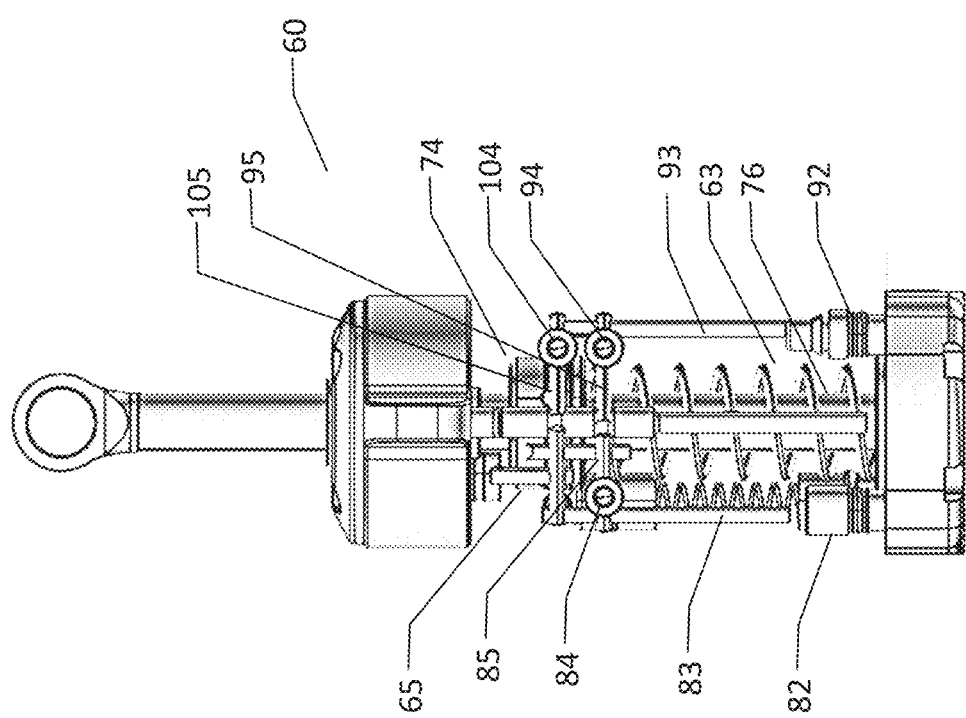
FIG. 6 is a side view of the hydraulic cylinder of FIG. 5 with portions removed to show internal structures.

FIG. 6 provides a side view of the hydraulic cylinder 60 with some features of the internal structure visible. The piston includes a piston head 65 that is movable in a cylinder bore 63 with the first fluid chamber above the piston head and the second fluid chamber below the piston head. The first fluid chamber is labeled as 74 to correspond to FIG. 3 and the second fluid chamber is labeled as 76 to correspond to FIG. 3. Springs or other biasing members may be provided in one or both chambers to bias the piston. As described with respect to FIG. 3, the extension hydraulic circuit includes a check valve 82. In FIG. 6, this check valve 82 is located adjacent the cylinder bore 63 at the lower end of the cylinder body, and is in fluid communication with the second fluid chamber 76. A fluid passage 83 extends upwardly to the resistance element 84 which is connected to the first fluid chamber 74 by another passage 85. For flexion resistance, another check valve 92 is provided at the lower end of the cylinder body and is in fluid communication with the second fluid chamber 76. As in FIG. 3, a fluid passage 93 connects the check valve 92 to resistance element 94 and a further passage 95 is in fluid communication with the first fluid chamber 74. The same passage 93 also connects to resistance element 104 and a further passage 105 extends from the resistance element to the mechanical switch (not shown in FIG. 6).

Figure 7:
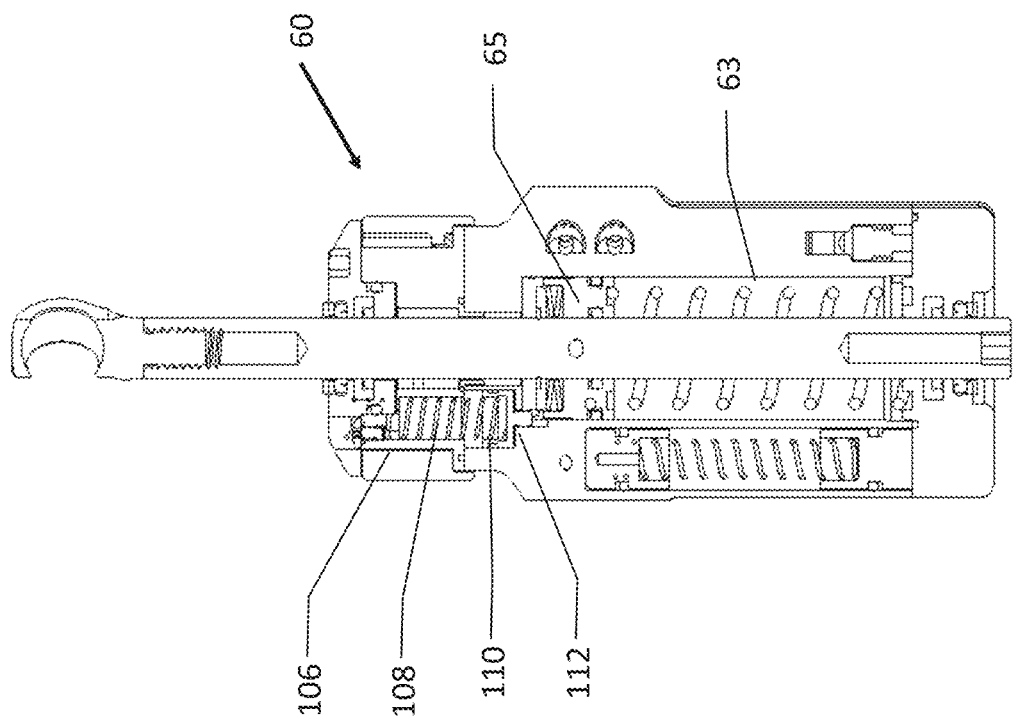
FIG. 7 is a cross-sectional view of the hydraulic cylinder of FIG. 5.

FIGS. 7 and 8 are cross-sectional views of the hydraulic cylinder 60 and the mechanical switch 106 is shown. The switch 106 has a body 108 and a plunger 110 extending downwardly from the body 108, with the lower end of the plunger being disposed in the upper end of the cylinder bore 63. In FIG. 7, the piston head 65 is spaced from the upper end of the bore 63 by a small amount and the plunger is extended, such that the switch 106 is in the released position and flow through passage 105 is blocked. In FIG. 8, the piston head 65 is at or near the upper end of the bore 63 and contacts the plunger 110 such that the plunger is depressed, putting the switch into the engaged position. A flow opening 112 is then defined under the plunger. Other arrangements may be provided which allow similar function.

Figure 9C:
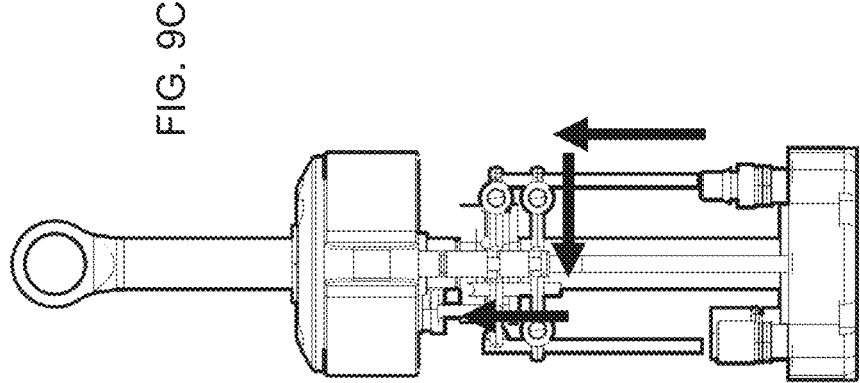
FIG. 9C is a partially cutaway view of the hydraulic cylinder indicating fluid flow.
Figure 9B:
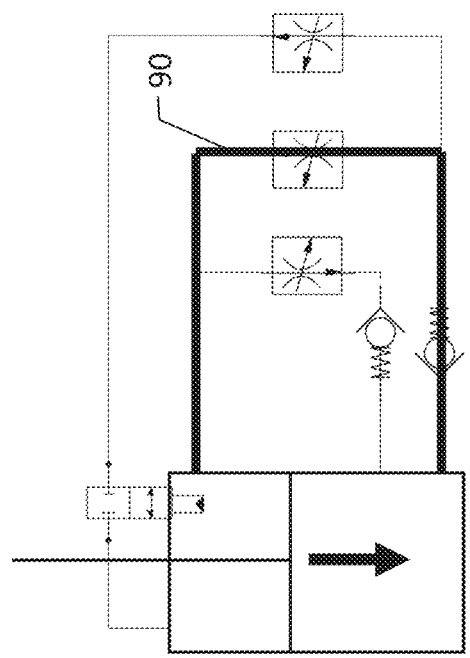
FIG. 9B is a schematic showing the fluid flow for the phases of FIG. 9A.
Figure 9A:
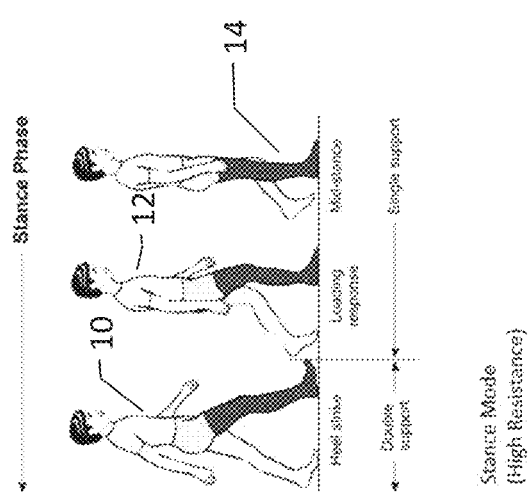
FIG. 9A is a schematic illustrating three phases of gait.

FIGS. 9A-C illustrate the operation of an embodiment of the resistance system when the knee is in a stance mode with high flexion resistance. FIG. 9A shows the positions 10, 12 and 14 during which high flexion resistance is needed. FIG. 9B shows the corresponding hydraulic resistance system schematic with the first flexion hydraulic circuit 90 highlighted. The direction of fluid flow and piston head movement is also shown. FIG. 9C is similar to FIG. 6 with arrows indicating the path of fluid flow in the stance mode.

Figures 10A, 10B, 10C:
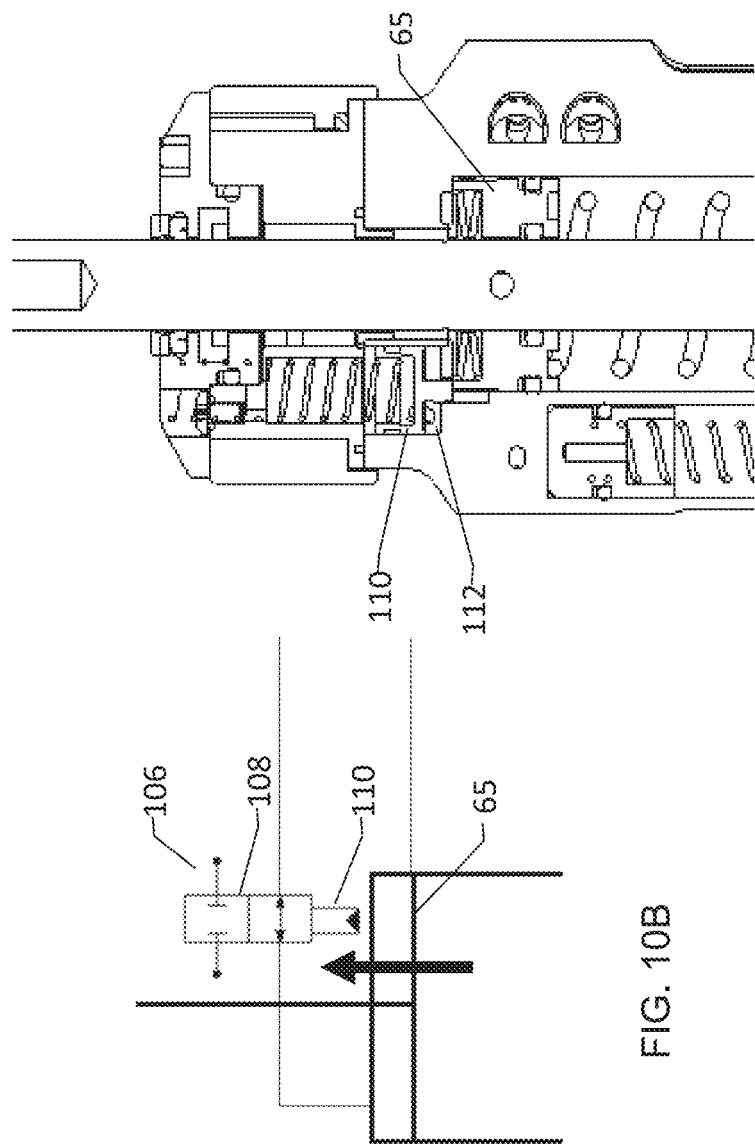
FIG. 10A is a schematic illustrating three phases of gait.
FIG. 10C is a is a cross-sectional view of a portion of the hydraulic cylinder showing the plunger depressed.
Figure 11D:
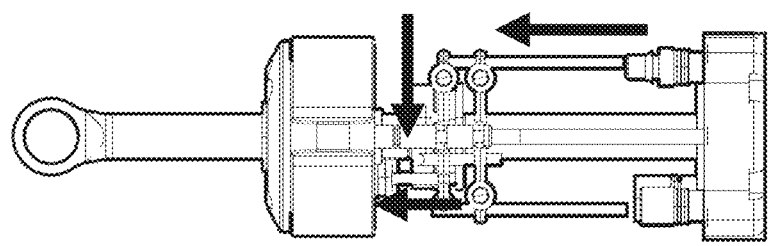
FIG. 11D is a partially cutaway view of the hydraulic cylinder indicating fluid flow.
Figure 11C:
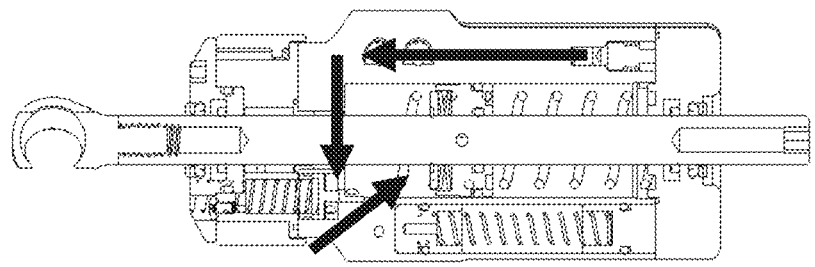
FIG. 11C is a cross-sectional view of the hydraulic cylinder showing fluid flow.
Figure 11B:
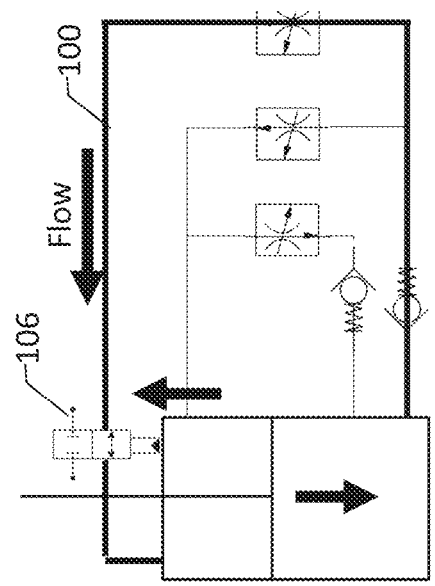
FIG. 11B is a schematic showing the fluid flow for the phases of FIG. 11A.
Figure 11A:
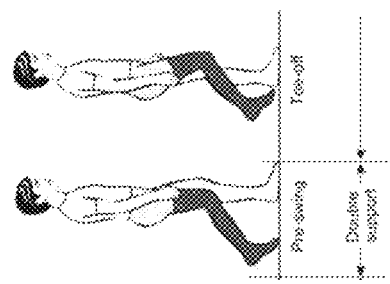
FIG. 11A is a schematic illustrating two phases of gait.

FIG. 10A shows the terminal stance position 16 and FIG. 1013 shows the mechanical switch 106 with the plunger depressed in the direction of the arrow. This is caused by the piston head 65 reaching a position corresponding to hyperextension of the knee. FIG. 10C is a view similar to FIG. 8 showing the plunger 110 depressed by the piston head 65 to uncover the passage 112. It is noted that the term "hyperextension" as used herein, when referring to the knee or leg, means a position beyond a "full extension" position of the knee or leg. The "full extension" position is the position in which the leg normally supports a user in a standing position and typically corresponds to the upper and lower leg being in a line with one another. However, the full extension position may be somewhat different from the upper and lower leg being in a line with one another. As such, "hyperextension" is a position that is at least slightly beyond the "full extension" position and is not necessarily a position beyond the position where the upper and lower portions are in a line. The hyperextension position may also be referred to as a predetermined extension position. The piston reaches a position where it may or may not contact the switch when the leg is in the full extension position and the piston depresses the plunger when the leg or knee is in the hyperextension position. The FIG. 11A-D illustrate the results of the mechanical switch 106 being engaged as the user moves into the flexion mode and the knee flexes. FIG. 11A shows the user in positions 18 and 20 wherein low resistance knee flexion occurs. FIG. 11B shows the schematic with the mechanical switch 106 engaged and arrows indicate that the piston is moving downwardly and low resistance fluid flow is passing through the secondary flexion hydraulic circuit 100. FIGS. 11C and 11D provide arrows showing the fluid flow in this mode.

Figure 12D:
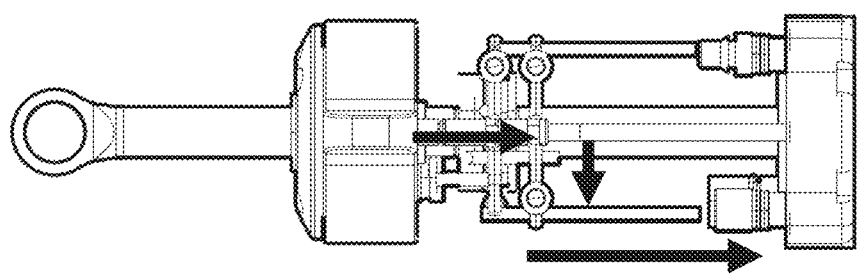
FIG. 12D is a partially cutaway view of the hydraulic cylinder indicating fluid flow.
Figure 12C:
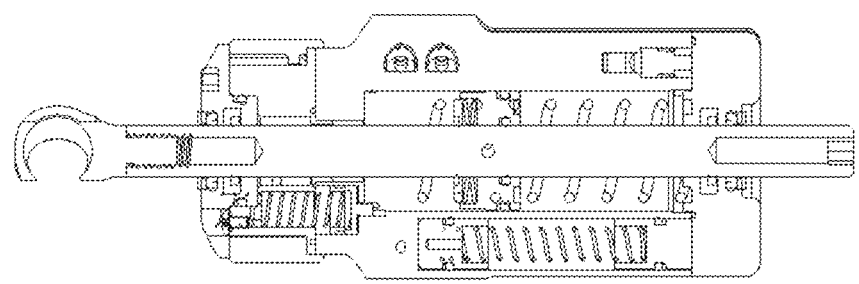
FIG. 12C is a cross-sectional view of the hydraulic cylinder.
Figure 12B:
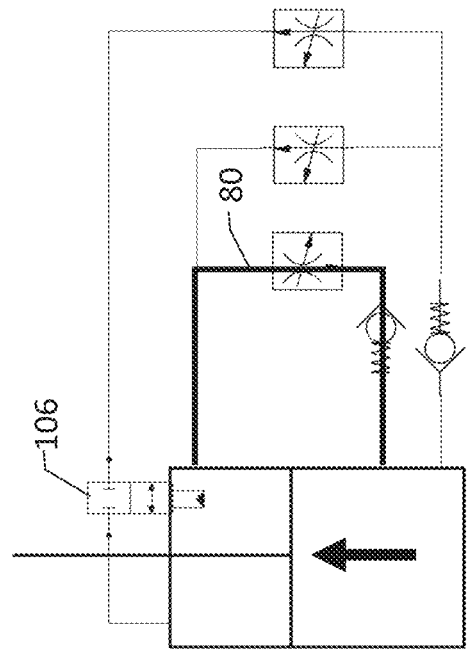
FIG. 12B is a schematic showing the fluid flow for the phases of FIG. 12A.
Figure 12A:
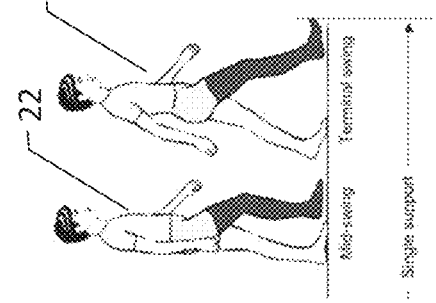
FIG. 12A is a schematic illustrating two phases of gait.

As described above, once flexion drops below a threshold, the switch 106 returns to the released position. FIG. 12A shows the user in positions 22 and 24 where flexion has ceased, the switch has released, and knee extension occurs. FIG. 12B shows the schematic with extension fluid flow occurring through extension circuit 80. FIG. 12C shows that the switch 106 is released and FIG. 12D shows the extension fluid flow through the circuit 80. It is noted that, because the switch is released, if the user places a load on the knee, the knee will provide a high level of resistance. The cycle then repeats from FIG. 9

Figures 13E, 13F:
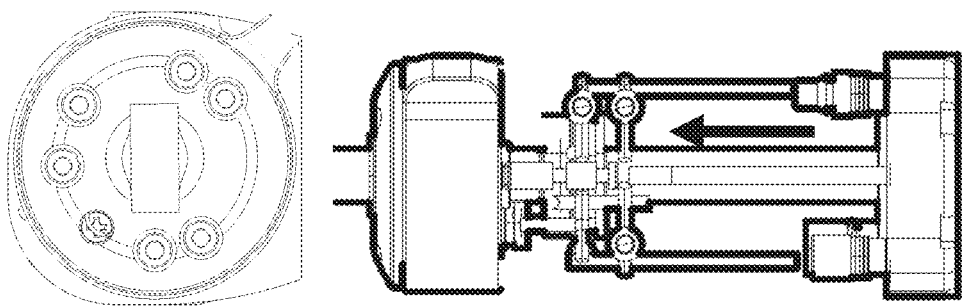
FIGS. 13A-13F are drawings showing three positions of a mode switch and the associated fluid flows.
Figures 13C, 13D:
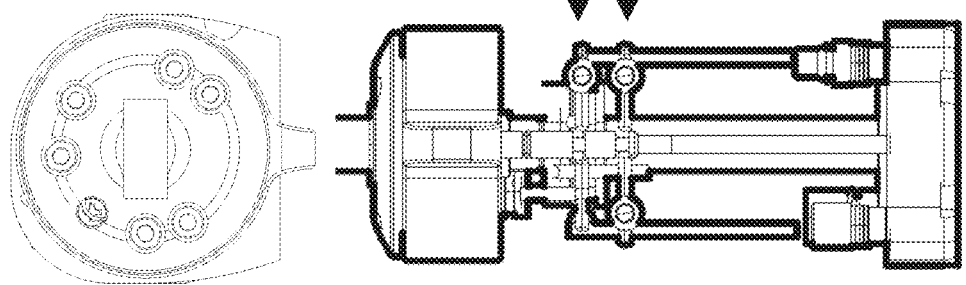
Figures 13A, 13B:
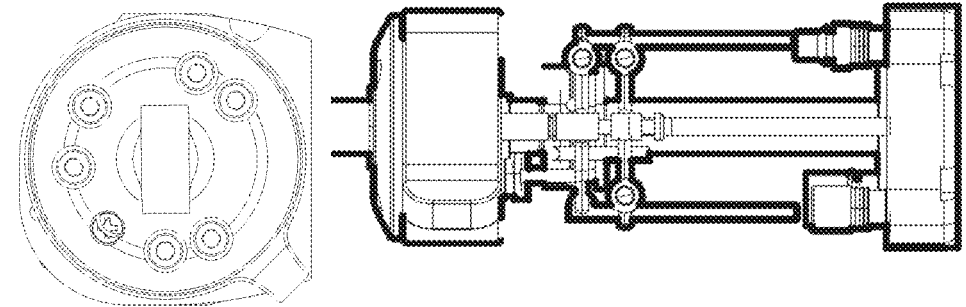

FIG. 13 illustrates various modes of operation which may be provided with some embodiments of the present invention. FIGS. 13A and B show the hydraulic resistance system in a locked position, in which the mode selection switch has been rotated clockwise. In this mode, the fluid passages are blocked, thereby locking the knee in position. FIGS. 13C and D show "normal" operation in which the knee operates as described above. The mode selection switch is in a middle position. FIGS. 13E and F show the mode selection switch rotated counterclockwise, which puts the knee into a free swing mode. In this position an additional fluid passageway is opened which allows fluid to flow freely between the first and second hydraulic chambers without being directed through any resistance element. This may be referred to as a bypass position.

Figure 14B:
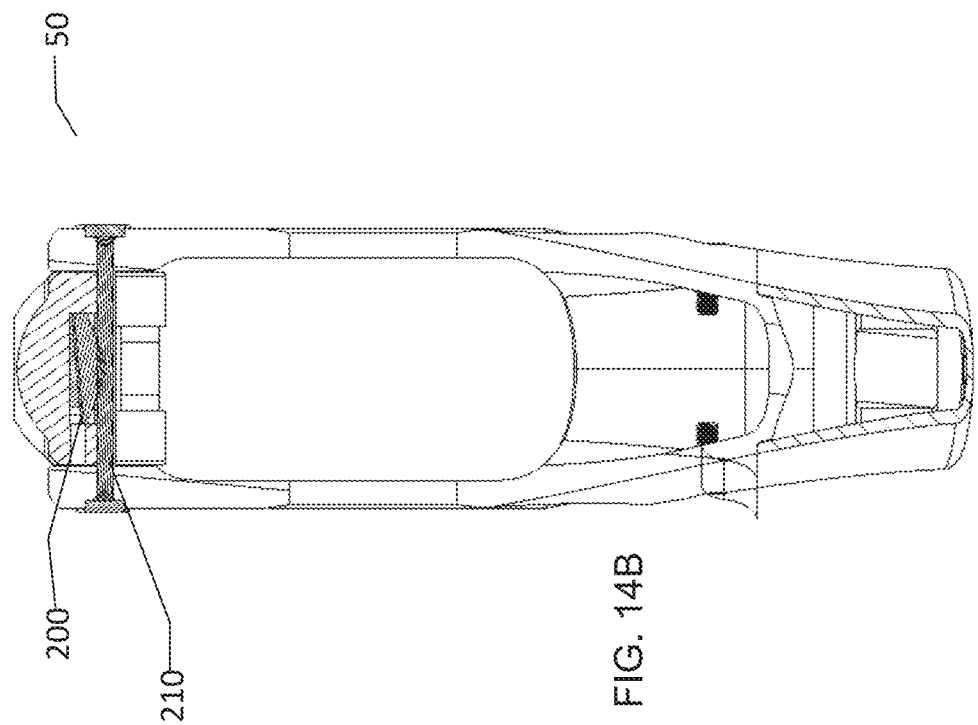
FIG. 14B is a cross-sectional front view of the knee of FIG. 14A.
Figure 14A:
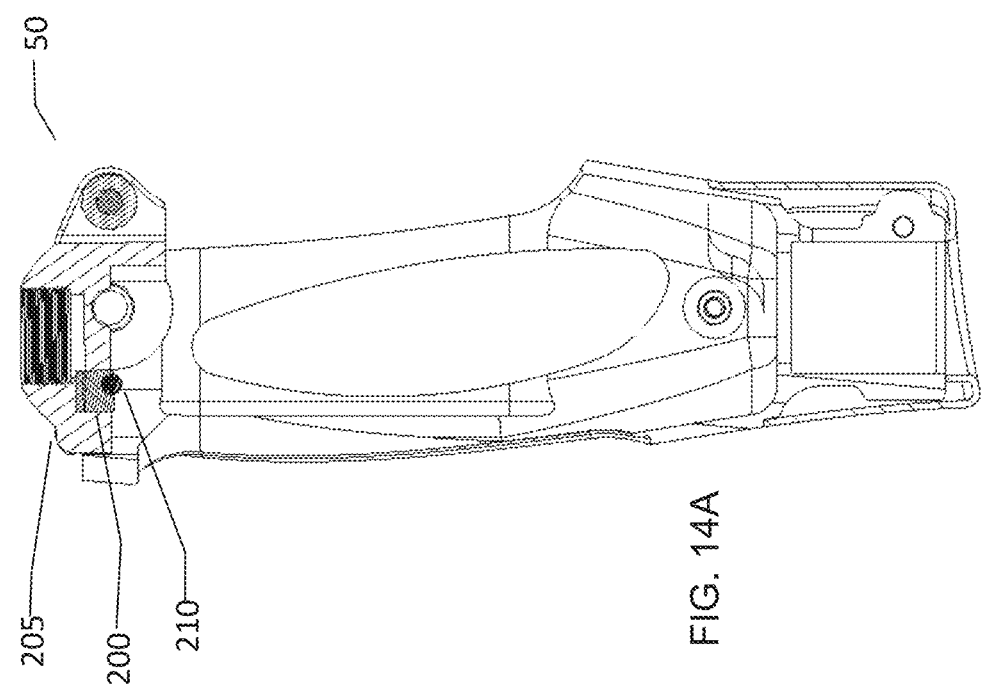
FIG. 14A is a cross-sectional side view of a knee showing an example of an adjustment mechanism.
Figure 15:
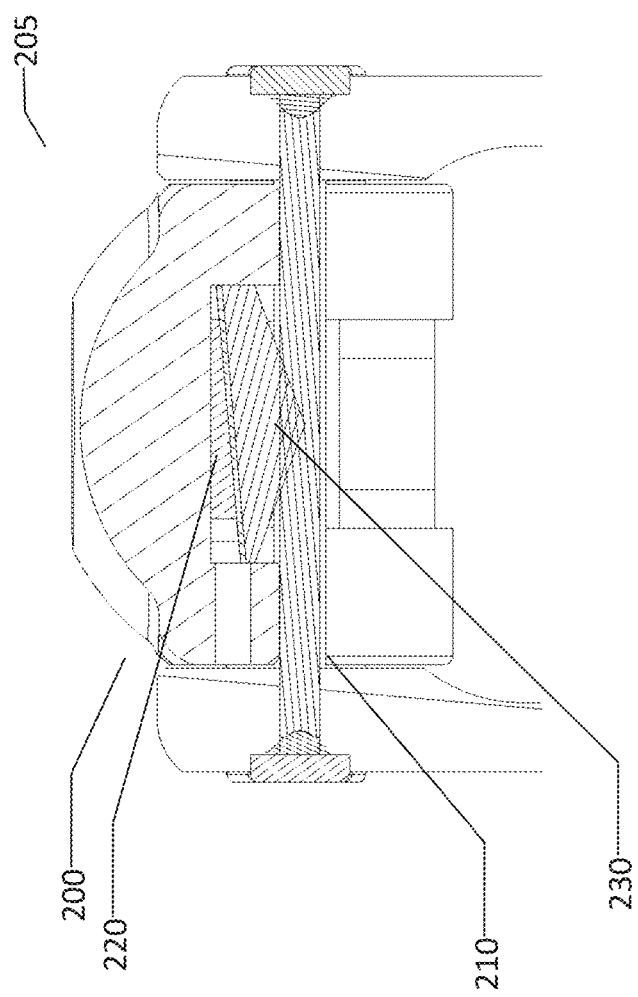
FIG. 15 is a detailed view of the mechanism of FIGS. 14A and 14B.

For some embodiments of the present invention, an adjustment mechanism may be provided for adjusting the amount of force necessary to engage the mechanical switch. One example of such an adjustment mechanism is illustrated in FIGS. 14A, 14B, and 15. FIG. 14A provides a side view of a knee assembly 50, wherein 205 indicates an upper bone subassembly and 210 indicates a physical stop, such as a stop pin, which restricts rotational movement of the upper bone assembly 205 by engaging an adjustable stop mechanism 200. FIG. 14B shows a front view of the knee assembly, 50, with the adjustable stop mechanism 200 and stop pin 210.

FIG. 15 shows the upper bone subassembly 205, composed of the adjustable stop assembly 200. Within the adjustable stop assembly is a wedge 220 which engages a bumper 230. The bumper then engages the stop pin 210 which limits rotational movement of the knee. As will be clear to those of skill in the art, by utilizing a wedge system, if the wedge 220 is move laterally, the bumper 230 would move along the vertical plane, which would either engage or disengage the stop pin 210. The use of the mechanism allows the user to adjust the forces required to activate hyperextension. Activating hyperextension is what allows the knee to flex at toe off, as shown in FIG. 10.

Other aspects of the prosthetic knee may also be adjustable. For example, the amount of force necessary to depress the plunger of the mechanical switch may be adjustable, as may the amount of travel necessary to switch to the second level of resistance.

As will be clear to those of skill in the art, the embodiments of the present invention described herein may be altered in various ways without departing from the scope of the invention. Any feature described for use with any embodiment may also be used with other embodiments, as will be clear to those of skill in the art. It is the following claims, including all equivalents, which define the scope of the present invention.

The invention claimed is:

1. A prosthetic knee, comprising:
an upper thigh portion;
a lower shin portion;
a joint connecting the upper and lower portions, the joint allowing the shin portion to articulate, between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and
a hydraulic resistance system operable to selectively provide hydraulic resistance to flexion and extension of the knee, the hydraulic resistance system comprising;
a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;
an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;

a flexion hydraulic circuit connecting the first and second fluid chambers, the flexion hydraulic circuit having;

a check valve operable to allow flow from the second fluid chamber to the first fluid chamber and to block flow from the first fluid chamber to the second fluid chamber; and a switchable resistance assembly including a mechanical switch, the mechanical switch having an engaged position and a released position, the switchable resistance assembly providing a first level of hydraulic resistance to flow from the second fluid chamber to the first fluid chamber when the mechanical switch is in the released position and a second level of hydraulic resistance to flow from the second fluid chamber to the first fluid chamber when the mechanical switch is in the engaged position, the second level being less than the first level;

the mechanical switch moving to the engaged position when the hydraulic resistance element reaches a predetermined extension position and moving back to the released position when flow from the second chamber to the first chamber falls below a predetermined threshold; and the mechanical switch comprising a body and a plunger, the plunger contacting the movable piston of the hydraulic resistance element when the hydraulic resistance element reaches the predetermined extension position.

2. The prosthetic knee according to claim 1, wherein the knee does not comprise any electronically controlled valves.

3. The prosthetic knee according to claim 1, wherein the hydraulic resistance element comprises a hydraulic cylinder with a cylinder body having a bore defined therein, the piston having a piston head separating the first fluid chamber from the second fluid chamber, and a piston rod connected to the upper thigh portion, the cylinder body being connected to the lower shin portion.

4. The prosthetic knee according to claim 1, wherein the flexion and extension resistance levels are adjustable.

5. The prosthetic knee according to claim 1, wherein the upper thigh portion comprises an upper bone subassembly.

6. The prosthetic knee according to claim 1, wherein the predetermined extension position is a hyperextension position.

7. The prosthetic knee according to claim 1, further comprising an adjustment mechanism for adjusting an amount of force required to engage the mechanical switch.

8. A prosthetic knee, comprising:
an upper thigh portion;
a lower shin portion;
a joint connecting the upper and lower portions, the joint allowing the shin portion to articulate between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and a hydraulic resistance system operable to selectively provide hydraulic resistance to flexion and extension of the knee, the hydraulic resistance system comprising;

a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;

an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;

a first flexion hydraulic circuit connecting the first and second fluid chambers, the first flexion hydraulic circuit having a check valve operable to allow flow from the second fluid chamber to the first fluid chamber and to block flow from the first fluid chamber to the second fluid chamber, the first flexion hydraulic circuit further having a resistance element operable to provide hydraulic resistance to the flow from the second fluid chamber to the first fluid chamber;

a second flexion hydraulic circuit connecting the first and second fluid chambers, the second flexion hydraulic circuit having a check valve operable to allow flow from the second fluid chamber to the first fluid chamber and to block flow from the first fluid chamber to the second fluid chamber, the second flexion hydraulic circuit further having a resistance element operable to provide hydraulic resistance to the flow from the second fluid chamber to the first fluid chamber;

the resistance element of the first flexion hydraulic circuit providing a first level of hydraulic resistance and the resistance element of the second flexion hydraulic circuit providing a second level of hydraulic resistance, the second level being less than the first level; and a mechanical switch having an engaged position and a released position, the mechanical switch in the engaged position operable to allow flow through the second flexion hydraulic circuit, thereby allowing flow during flexion through the second flexion circuit, the mechanical switch in the released position blocking the second flexion hydraulic circuit, thereby limiting flow during flexion to the first flexion hydraulic circuit, the mechanical switch moving to the engaged position when the hydraulic resistance element reaches a predetermined extension position and moving back to the released position when flow from the second chamber to the first chamber falls below a predetermined threshold;

wherein the mechanical switch comprises a body and a plunger, the plunger contacting the movable piston of the hydraulic resistance element when the hydraulic resistance element reaches the predetermined extension position.

9. The prosthetic knee according to claim 8, wherein the knee does not comprise any electronically controlled valves.

10. The prosthetic knee according to claim 8, wherein the hydraulic resistance element comprises a hydraulic cylinder with a cylinder body having a bore defined therein, the piston having a piston head separating the first fluid chamber from the second fluid chamber, and a piston rod connected to the upper thigh portion, the cylinder body being connected to the lower shin portion.

11. The prosthetic knee according to claim 8, wherein the flexion and extension resistance levels are adjustable.

12. The prosthetic knee according to claim 8, wherein the upper thigh portion comprises an upper bone subassembly.

13. The prosthetic knee according to claim 8, wherein the predetermined extension position is a hyperextension position.

14. The prosthetic knee according to claim 8, further comprising an adjustment mechanism for adjusting an amount of force required to engage the mechanical switch.

15. A method of controlling a prosthetic knee, comprising:
   providing a prosthetic knee, comprising:
      an upper thigh portion;
      a lower shin portion;
      a joint connecting the upper and lower portions, the joint allowing the shin portion to articulate between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and
      a hydraulic resistance element operable to selectively provide hydraulic resistance to flexion and extension of the knee, the hydraulic resistance system comprising;
         a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;
         an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;
         a flexion hydraulic circuit connecting the first and second fluid chambers, the flexion hydraulic circuit having;
            a check valve operable to allow flow from the second fluid chamber to the first fluid chamber and to block flow from the first fluid chamber to the second fluid chamber; and
            a switchable resistance assembly including a mechanical switch, the mechanical switch having an engaged position and a released position, the switchable resistance assembly providing a first level of hydraulic resistance to flow from the second fluid chamber to the first fluid chamber when the mechanical switch is in the released position and a second level of hydraulic resistance to flow from the second fluid chamber to the first fluid chamber when the mechanical switch is in the engaged position, the second level being less than the first level;
   moving the mechanical switch to the engaged position when the hydraulic resistance element reaches a predetermined extension position and moving the mechanical switch back to the released position when flow from the second chamber to the first chamber falls below a predetermined threshold;
   wherein the mechanical switch comprises a body and a plunger, the plunger contacting the movable piston of the hydraulic resistance element when the hydraulic resistance element reaches the predetermined extension position.

16. A prosthetic knee, comprising:
   an upper thigh portion;
   a lower shin portion;
   a joint connecting the upper and lower portions, the joint allowing the shin portion to articulate, between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and
   a hydraulic resistance system operable to selectively provide hydraulic resistance to flexion and extension of the knee, the hydraulic resistance system comprising;
      a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;
      an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;
      a flexion hydraulic circuit connecting the first and second fluid chambers, the flexion hydraulic circuit having;
         a check valve operable to allow flow from the second fluid chamber to the first fluid chamber and to block flow from the first fluid chamber to the second fluid chamber; and
         a switchable resistance assembly including a mechanical switch, the mechanical switch having an engaged position and a released position, the switchable resistance assembly providing a first level of hydraulic resistance to flow from the second fluid chamber to the first fluid chamber when the mechanical switch is in the released position and a second level of hydraulic resistance to flow from the second fluid chamber to the first fluid chamber when the mechanical switch is in the engaged position, the second level being less than the first level;

the mechanical switch moving to the engaged position when the hydraulic resistance element reaches a predetermined extension position and moving back to the released position when flow from the second chamber to the first chamber falls below a predetermined threshold, the predetermined extension position being a hyperextension position.

17. The prosthetic knee according to claim 16, wherein the knee does not comprise any electronically controlled valves.

18. The prosthetic knee according to claim 16, wherein the hydraulic resistance element comprises a hydraulic cylinder with a cylinder body having a bore defined therein, a the piston having a piston head separating the first fluid chamber from the second fluid chamber, and a piston rod connected to the upper thigh portion, the cylinder body being connected to the lower shin portion.

19. The prosthetic knee according to claim 16, wherein the flexion and extension resistance levels are adjustable.

20. The prosthetic knee according to claim 16, wherein the upper thigh portion comprises an upper bone subassembly.

21. The prosthetic knee according to claim 16, further comprising an adjustment mechanism for adjusting an amount of force required to engage the mechanical switch.

22. A prosthetic knee, comprising:
an upper thigh portion;
a lower shin portion;
a joint connecting the upper and lower portions, the joint allowing the shin portion to articulate, between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and
a hydraulic resistance system operable to selectively provide hydraulic resistance to flexion and extension of the knee, the hydraulic resistance system comprising;
a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;
an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;
a flexion hydraulic circuit connecting the first and second fluid chambers, the flexion hydraulic circuit having;

a check valve operable to allow flow from the second fluid chamber to the first fluid chamber and to block flow from the first fluid chamber to the second fluid chamber;
a switchable resistance assembly including a mechanical switch, the mechanical switch having an engaged position and a released position, the switchable resistance assembly providing a first level of hydraulic resistance to flow from the second fluid chamber to the first fluid chamber when the mechanical switch is in the released position and a second level of hydraulic resistance to flow from the second fluid chamber to the first fluid chamber when the mechanical switch is in the engaged position, the second level being less than the first level; and
an adjustment mechanism for adjusting an amount of force required to engage the mechanical switch;
the mechanical switch moving to the engaged position when the hydraulic resistance element reaches a predetermined extension position and moving back to the released position when flow from the second chamber to the first chamber falls below a predetermined threshold.

23. The prosthetic knee according to claim 22, wherein the knee does not comprise any electronically controlled valves.

24. The prosthetic knee according to claim 22, wherein the hydraulic resistance element comprises a hydraulic cylinder with a cylinder body having a bore defined therein, a the piston having a piston head separating the first fluid chamber from the second fluid chamber, and a piston rod connected to the upper thigh portion, the cylinder body being connected to the lower shin portion.

25. The prosthetic knee according to claim 22, wherein the flexion and extension resistance levels are adjustable.

26. The prosthetic knee according to claim 22, wherein the upper thigh portion comprises an upper bone subassembly.

27. A prosthetic knee, comprising:
an upper thigh portion;
a lower shin portion;
a joint connecting the upper and lower portions, the joint allowing the shin portion to articulate between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and
a hydraulic resistance system operable to selectively provide hydraulic resistance to flexion and extension of the knee, the hydraulic resistance system comprising;
a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;
an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;

a first flexion hydraulic circuit connecting the first and second fluid chambers, the first flexion hydraulic circuit having a check valve operable to allow flow from the second fluid chamber to the first fluid chamber and to block flow from the first fluid chamber to the second fluid chamber, the first flexion hydraulic circuit further having a resistance element operable to provide hydraulic resistance to the flow from the second fluid chamber to the first fluid chamber;

a second flexion hydraulic circuit connecting the first and second fluid chambers, the second flexion hydraulic circuit having a check valve operable to allow flow from the second fluid chamber to the first fluid chamber and to block flow from the first fluid chamber to the second fluid chamber, the second flexion hydraulic circuit further having a resistance element operable to provide hydraulic resistance to the flow from the second fluid chamber to the first fluid chamber;

the resistance element of the first flexion hydraulic circuit providing a first level of hydraulic resistance and the resistance element of the second flexion hydraulic circuit providing a second level of hydraulic resistance, the second level being less than the first level; and a mechanical switch having an engaged position and a released position, the mechanical switch in the engaged position operable to allow flow through the second flexion hydraulic circuit, thereby allowing flow during flexion through the second flexion circuit, the mechanical switch in the released position blocking the second flexion hydraulic circuit, thereby limiting flow during flexion to the first flexion hydraulic circuit, the mechanical switch moving to the engaged position when the hydraulic resistance element reaches a predetermined extension position and moving back to the released position when flow from the second chamber to the first chamber falls below a predetermined threshold, the predetermined extension position being a hyperextension position.

28. The prosthetic knee according to claim 27, wherein the knee does not comprise any electronically controlled valves.

29. The prosthetic knee according to claim 27, wherein the hydraulic resistance element comprises a hydraulic cylinder with a cylinder body having a bore defined therein, a the piston having a piston head separating the first fluid chamber from the second fluid chamber, and a piston rod connected to the upper thigh portion, the cylinder body being connected to the lower shin portion.

30. The prosthetic knee according to claim 27, wherein the flexion and extension resistance levels are adjustable.

31. The prosthetic knee according to claim 27, wherein the upper thigh portion comprises an upper bone subassembly.

32. The prosthetic knee according to claim 27, further comprising an adjustment mechanism for adjusting an amount of force required to engage the mechanical switch.

33. A prosthetic knee, comprising:
an upper thigh portion;
a lower shin portion;
a joint connecting the upper and lower portions, the joint allowing the shin portion to articulate between an extended position wherein the thigh portion and the shin portion are generally aligned along a leg axis and a bent position wherein the shin portion is angled rearwardly with respect to the thigh portion, wherein movement from the extended position toward the bent position is defined as flexion and movement from the bent position toward the extended position is defined as extension; and a hydraulic resistance system operable to selectively provide hydraulic resistance to flexion and extension of the knee, the hydraulic resistance system comprising;

a hydraulic resistance element having a movable piston defining a first fluid chamber on a first side of the piston and a second fluid chamber on a second side of the piston, a size of the first chamber increasing and a size of the second chamber reducing during flexion and the size of the first chamber decreasing and the second chamber increasing during extension;

an extension hydraulic circuit connecting the first and second fluid chambers, the extension hydraulic circuit having a check valve operable to allow flow from the first fluid chamber to the second fluid chamber and to block flow from the second fluid chamber to the first fluid chamber, the extension hydraulic circuit further having a resistance element operable to provide hydraulic resistance to the flow from the first fluid chamber to the second fluid chamber;

a first flexion hydraulic circuit connecting the first and second fluid chambers, the first flexion hydraulic circuit having a check valve operable to allow flow from the second fluid chamber to the first fluid chamber and to block flow from the first fluid chamber to the second fluid chamber, the first flexion hydraulic circuit further having a resistance element operable to provide hydraulic resistance to the flow from the second fluid chamber to the first fluid chamber;

a second flexion hydraulic circuit connecting the first and second fluid chambers, the second flexion hydraulic circuit having a check valve operable to allow flow from the second fluid chamber to the first fluid chamber and to block flow from the first fluid chamber to the second fluid chamber, the second flexion hydraulic circuit further having a resistance element operable to provide hydraulic resistance to the flow from the second fluid chamber to the first fluid chamber;

the resistance element of the first flexion hydraulic circuit providing a first level of hydraulic resistance and the resistance element of the second flexion hydraulic circuit providing a second level of hydraulic resistance, the second level being less than the first level; and a mechanical switch having an engaged position and a released position, the mechanical switch in the engaged position operable to allow flow through the second flexion hydraulic circuit, thereby allowing flow during flexion through the second flexion circuit, the mechanical switch in the released position blocking the second flexion hydraulic circuit, thereby limiting flow during flexion to the first flexion hydraulic circuit, the mechanical switch moving to the engaged position when the hydraulic resistance element reaches a predetermined extension position and moving back to the released position when flow from the second chamber to the first chamber falls below a predetermined threshold; and an adjustment mechanism for adjusting an amount of force required to engage the mechanical switch.

34. The prosthetic knee according to claim 33, wherein the knee does not comprise any electronically controlled valves.

35. The prosthetic knee according to claim 33, wherein the hydraulic resistance element comprises a hydraulic cylinder with a cylinder body having a bore defined therein, a the piston having a piston head separating the first fluid chamber from the second fluid chamber, and a piston rod connected to the upper thigh portion, the cylinder body being connected to the lower shin portion.

36. The prosthetic knee according to claim 33, wherein the flexion and extension resistance levels are adjustable.

37. The prosthetic knee according to claim 33, wherein the upper thigh portion comprises an upper bone subassembly.

* * * * *